(12) United States Patent
Haar (10) Patent No.: US 8,821,442 B2
(45) Date of Patent: Sep. 2, 2014

(54) INFUSION SYSTEM

(75) Inventor: Hans-Peter Haar, Wiesloch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 289 days.

(21) Appl. No.: 12/542,047

(22) Filed: Aug. 17, 2009

(65) Prior Publication Data

US 2010/0211011 A1    Aug. 19, 2010

Related U.S. Application Data

(63) Continuation of application No. PCT/EP2008/000695, filed on Jan. 30, 2008.

(30) Foreign Application Priority Data

Feb. 24, 2007    (EP) .................................. 07003826

(51) Int. Cl.
*A61M 1/00* (2006.01)
*A61M 5/142* (2006.01)
*H02J 7/00* (2006.01)
*A61M 5/168* (2006.01)
*A61B 5/145* (2006.01)
*A61M 5/145* (2006.01)

(52) U.S. Cl.
CPC ....... *A61M 5/14248* (2013.01); *A61M 5/16854* (2013.01); *A61M 2205/8206* (2013.01); *A61M 2205/3561* (2013.01); *A61M 2209/086* (2013.01); *A61B 5/14532* (2013.01); *A61M 2209/045* (2013.01); *A61M 2205/3592* (2013.01); *A61M 2205/52* (2013.01); *A61M 2205/3569* (2013.01); *A61M 5/14566* (2013.01)
USPC ............................ 604/151; 320/107; 320/128

(58) Field of Classification Search
CPC ................. A61M 2209/086; A61M 2209/045; A61M 5/14566; A61M 2205/8206
USPC ................... 604/131, 151–155; 320/124–128
See application file for complete search history.

(56) References Cited

U.S. PATENT DOCUMENTS 3,802,430 A  *  4/1974  Schwebel et al. ............... 604/69
4,573,994 A      3/1986  Fischell et al.
(Continued)

FOREIGN PATENT DOCUMENTS

CN          1681544 A     10/2005
DE          20017371 U1    1/2001
(Continued)

OTHER PUBLICATIONS

Translation of Steffen et al DE20017371U1.*
English Translation of the International Preliminary Report on Patentability from corresponding PCT/EP2008/000695.

* cited by examiner

*Primary Examiner* — Matthew F Desanto
*Assistant Examiner* — Jenna Zhang
(74) *Attorney, Agent, or Firm* — Roche Diagnostics Operations, Inc.

(57) ABSTRACT

Disclosed is an infusion system for administering a liquid medicament, particularly insulin. Said infusion system comprises a cannula support unit which is properly attached to a patient's body, an infusion cannula to be inserted into the patient's body, and a pump unit that can be connected to the cannula support unit and encompasses a pump, a battery for supplying power to the pump, and a storage volume for the medicament that is to be administered. The pump unit and the cannula support unit are adapted to one another in such a way that the pump unit rests against the cannula support unit once the pump unit has been connected to the cannula support unit. The disclosed infusion system also comprises a charging station for the pump unit in order to recharge the battery of the pump unit.

16 Claims, 5 Drawing Sheets

(56) References Cited

U.S. PATENT DOCUMENTS

| | | | |
|---|---|---|---|
| 4,871,351 A * | 10/1989 | Feingold | 604/66 |
| 6,416,495 B1 * | 7/2002 | Kriesel et al. | 604/132 |
| 2003/0100864 A1 | 5/2003 | Bendsen et al. | |
| 2004/0059316 A1 * | 3/2004 | Smedegaard | 604/890.1 |
| 2005/0107899 A1 | 5/2005 | Steffen | |
| 2005/0192561 A1 * | 9/2005 | Mernoe | 604/890.1 |
| 2006/0074381 A1 * | 4/2006 | Malave et al. | 604/93.01 |
| 2007/0219496 A1 * | 9/2007 | Kamen et al. | 604/131 |

FOREIGN PATENT DOCUMENTS

| | | |
|---|---|---|
| DE | 10048220 A1 | 5/2001 |
| WO | 92/16990 A1 | 10/1992 |
| WO | 01/72358 A1 | 10/2001 |
| WO | 2004/009160 A1 | 1/2004 |
| WO | 2004/026375 A1 | 4/2004 |
| WO | 2004/098390 A2 | 11/2004 |

INFUSION SYSTEM

REFERENCE

This application is a continuation of PCT/EP2008/000695 filed 30 Jan. 2008 which is based on and claims priority to European Patent Application No. EP 07003826.0 filed 24 Feb. 2007, which are hereby incorporated by reference.

FIELD

The invention relates to an infusion system for administering a liquid medicinal agent.

BACKGROUND

Many diabetics depend on external doses of insulin for regulation of their blood glucose level. Usually, these insulin doses are administered several times daily in the form of injections. From a medical point of view, though, continuous insulin doses are advantageous, such as are feasible using, for example, the infusion system known from WO 2004/098390 A2. Disadvantages of known infusion systems include, on the one hand, that the comfort of wear is experienced by many users as being insufficient and, on the other hand, the considerable costs which exceed by far the costs of a treatment by multiple daily insulin injections.

SUMMARY

It is therefore the object of the invention to devise a way in which the costs of an infusion system can be lowered and the user comfort can be increased.

The infusion system according to an embodiment of the invention comprises a cannula carrier unit and a pump unit that can be attached to it, which, when used according to purpose, are carried together by a user under the clothing. In an infusion system embodiment, the pump unit and the cannula carrier unit can be adapted to each other such that the pump unit rests against the cannula carrier unit once the pump unit is attached to the cannula carrier unit, though this is not imperative. For example, the pump unit can just as well be carried on the body at a distance from the cannula carrier unit using a tubing as connecting line. Because the cannula carrier unit and the pump unit can be carried under the clothing, a high comfort of wear is attained, since the medicinal agent to be administered can be guided into the body of the patient via a short path from the pump unit via the infusion cannula of the cannula carrier unit of the cannula carrier unit resting against it. Long infusion tubing, which is experienced as annoying and bothersome by most users, can be avoided by this means. Moreover, long infusion tubing is associated with the risk of the transport of liquid being disturbed by mechanical movement and strain.

In this context, the modular design of an infusion system according to the invention allows for cost-efficient realization thereof. This is the case since the storage volume of the pump unit of an infusion system according to the invention can be refilled time and again with the medicinal agent to be administered and can therefore be used multiply. Typically, the manufacturing costs of a cannula carrier unit including the infusion cannula for puncturing into the body of a patient are only a fraction of the manufacturing costs of a pump unit. The cannula carrier unit can therefore be designed as a hygienic disposable article without significantly increasing the cost of the system.

For supplying energy to the pump unit, the infusion system is provided with a rechargeable battery that can be recharged by a charging station that is adapted to the pump unit. The rechargeable battery is preferably recharged by inductive coupling with the charging station. This is preferable, because, by this means, possible sites of leakage through which moisture or dirt might enter into the pump unit can be minimized.

As mentioned above, the pump unit has a storage volume for the medicinal agent to be administered. This storage volume can be less than 2 ml, such as less than 1.5 ml, and in particular no more than 1 ml. This measure is seemingly disadvantageous in that the stock of medicinal agent that can be stored in the storage volume is sufficient for only approximately half a day or only several hours, for example if the infusion system is used for administering insulin to a diabetic.

Once the stock of medicinal agent of a pump unit of an infusion system according to the invention is spent, the storage volume can be replenished. The cannula carrier unit can remain on the body of the patient during this process such that there is no need for the complex and, to the patient, painful placement of a new infusion cannula. Therefore, an infusion cannula can be used for a longer period of time in an infusion system according to the invention, e.g. three to four days, and remain in place in the body of the patient despite the small storage volume of the pump unit.

As a matter of principle, the pump unit can be designed such that the storage volume can be replenished without needing to be uncoupled from the cannula carrier unit, for example by exchanging a medicinal agent container that is contained in the storage volume. However, the pump unit can be uncoupled from the cannula carrier unit when all of the medicinal agent contained in the storage volume is administered. After replenishing the storage volume, the pump unit can again be coupled to the cannula carrier unit. It is particularly favorable in this context for a patient to use two pump units in an alternating manner such that a pump unit having a filled storage volume can be attached to the cannula carrier unit right after uncoupling a pump unit whose storage volume is spent.

Accordingly, what is achieved by having a small storage volume of the pump unit in the infusion system according to the invention is that a patient has to carry only a relatively small and compact device on the body. This is extraordinarily favorable for the comfort of wear and far outweighs the seeming disadvantage of having to fill the pump units more frequently. Therefore, the infusion system according to the invention allows extraordinarily high user comfort to be attained despite the relatively low cost.

One embodiment of an infusion system provides the charging station to be set up for charging the tank containing the medicinal agent to be administered. By this means, a user can easily charge/replenish both the rechargeable battery of the pump unit and its storage volume. It is particularly favorable in this context to use a charging station in combination with two pump units that are carried on the body in an alternating manner such that, at all times, one pump unit is coupled to the charging station and charged thereon. Therefore, one aspect of the invention relates to a device set for an infusion system having two pump units, which each comprise a pump, a rechargeable battery for supplying energy to the pump, and a storage volume for the medicinal agent to be administered, as well as having one charging station to which one pump unit each can be coupled for charging the rechargeable battery and for filling the charging station.

An alternative embodiment of an infusion system envisions the storage volume of the pump unit to be provided for receiving two medicinal agent containers. By this means, the pump can first administer the content of the first medicinal agent container and subsequently the content of the second medicinal agent container. As soon as the first medicinal agent container is empty, a user can exchange it for a full container. The advantage of having a pump unit with a storage volume for receiving two medicinal agent containers in contrast to a pump unit with a storage volume for receiving a larger medicinal agent container is that the user can freely select the point in time at which he changes an empty container over a time window of several hours. Once the first container is empty, a user has convenient time to exchange said container for a full container since it suffices to effect the exchange before the second container is empty also. In contrast, when a pump unit having only a single medicinal agent container is used, the exchange must be effected either right after the container is emptied completely or expensive agent must be wasted by exchanging an incompletely emptied container for a full one. Therefore, one aspect of the invention relates to a pump unit for an infusion system, whereby the pump unit is designed to receive two exchangeable medicinal agent containers.

BRIEF DESCRIPTION OF THE DRAWINGS

Further details and advantages of the invention are explained on the basis of embodiments referring to the appended drawings. Identical and corresponding components are identified by the same reference numbers. The features of the examples illustrated in the following can be made the subject matter of claims either alone or in combination.

In the figures.

DETAILED DESCRIPTION

Figure 1:
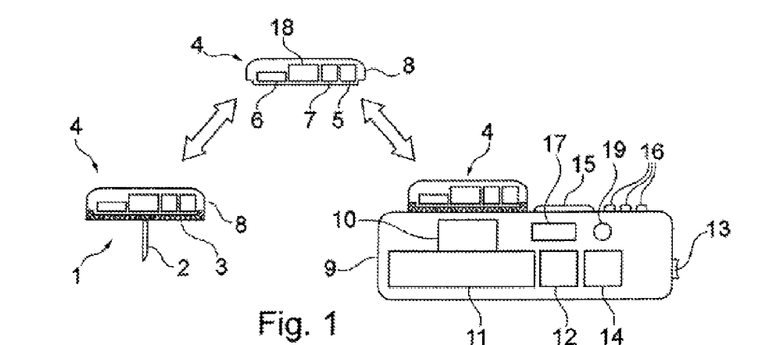
FIG. 1 shows a schematic view of an embodiment of an infusion system embodiment having a cannula carrier unit, a pump unit, and a charging station.

FIG. 1 shows a schematic view of an embodiment of an infusion system for administering a liquid medicinal agent, for example insulin. The infusion system includes a cannula carrier unit 1 configured to be secured to the body of a patient, and an infusion cannula 2 for puncturing into the body of the patient. The embodiment of the cannula carrier unit 1 shown has a contact surface 3, for example a pad, that can be coated with adhesive on its underside to be secured more easily on the body of a patient.

The infusion cannula 2 can, for example, be a hollow needle that is to be punctured into the body of the patient using a pointed end and subsequently serves for guiding the liquid medicinal agent. However, the infusion cannula 2 can just as well be a flexible plastic tube, made from Teflon for example, that is inserted into the body by, means of a hard support or carrier cannula. The support or carrier cannula can, for example, be made of steel and have a V-shaped cross-section such that the flexible infusion cannula rests in a groove formed by the support or carrier cannula during the puncture. The pointed support or carrier cannula can be removed after insertion of the flexible infusion cannula 2.

The infusion system further includes a pump unit 4 that can be connected to the cannula carrier unit 1 in a positive-fit manner. The exemplary embodiment of the pump unit 4 shown contains a pump 5, a rechargeable battery 6 for supplying energy to the pump 5, and a storage volume 7 for the medicinal agent to be administered. As shown in FIG. 1, the pump unit 4 has a housing 8 that rests against the cannula carrier unit 1 after the pump unit 4 is attached to the cannula carrier unit 1.

Connecting the pump unit 4 to a cannula carrier unit 1 creates a small and compact device that can be carried on the body comfortably by a patient and administers a liquid medicinal agent to the patient. The path from the storage volume of the pump unit 4 to the cannula is advantageously short in this context, on the order of no more than a few centimeters. During a first start-up after attaching the cannula carrier unit on the body of the patient, only a very small volume of air needs to be displaced from a liquid line leading from the storage volume 7 to the infusion cannula 2 (see FIG. 4) such that, even with pumping power being low, the medicinal agent can already be guided into the body of the patient after a very short period of time.

The pump unit 4 can be detached from a cannula carrier unit 1 that is secured to the body of the patient and can be coupled to a charging station 9 that is also part of the infusion system in order to charge its rechargeable battery 6 and refill its storage volume 7. An exemplary embodiment of the charging station 9 is also shown schematically in FIG. 1.

Increased user comfort can be attained in this context by a patient using two pump units 4 attaching them in an alternating manner to the cannula carrier unit 1 and the charging station 9. By this means, a pump unit 4 is recharged by the charging station 9 while the other pump unit 4 is attached to a cannula carrier unit 1 and used for infusion.

The storage volume 7 of the pump unit 4 is less than 2 ml and in some embodiments no more than 1 ml. By this means, the pump unit can be designed to be particularly small and compact, since the pump unit 4, according to its purpose, is carried by a patient on the body under the clothing together with a cannula carrier unit and should be as inconspicuous as possible. Although having a smaller storage volume 7 necessitates the medicinal agent to be refilled more frequently, this only seems to be a disadvantage in the infusion system shown since the pump unit 4 is easy to uncouple from the cannula carrier unit 1 and to replace by a filled pump unit 4.

The rechargeable battery 6 contained in the pump unit 4 is incorporated into the pump unit 4 such as to be inaccessible to a user, for example it is integrated into the housing 8 of the pump unit 4. This measure reduces potential sites of leakage through which moisture and dirt might enter into the pump unit can be minimized. Particularly well-suited are, in particular, lithium-polymer rechargeable batteries, which are designed in the form of flexible edge-sealed bags and can therefore be adapted easily to the shape of a space that is available in the pump unit 4 for incorporation thereof. Therefore, pump unit 4 can be provided to be especially compact using lithium-polymer rechargeable batteries. In order to be able to provide the rechargeable battery 6 and therefore the pump unit 4 as small and compact as possible, the rechargeable battery 6 preferably has an energy storage capacity for approximately 4 to 12 hours only, for example of 500 Joules, and in some embodiments no more than 200 Joules.

The exemplary embodiment of a charging station 9 shown schematically in FIG. 1 has a receiving compartment 10 for a storage container containing the medicinal agent to be administered. To refill the storage volume 7 of a pump unit 4 that is coupled to the charging station 9, medicinal agent is pumped from a storage container that is inserted in the receiving compartment 10 into the storage volume 7 of the pump unit. As a matter of principle, the pump 5 of the coupled pump unit 4 can be used for this purpose; however, the charging station 9 preferably has a separate pump 11 for this purpose.

The charging station 9 contains a powerful energy storing facility 12, for example a replaceable battery or, preferably, a rechargeable battery that supplies electrical energy to the rechargeable battery 6 of the pump station 4 to recharge the rechargeable battery 6 of the pump station 4. By this means, the charging station 9 can be carried along by a patient, for example in a jacket pocket or purse, and used "on the road". Preferably, the storage capacity of the energy storing facility 12 is at least 10-times larger than that of the rechargeable battery 6 of the pump unit 4 such that the charging station can be used for several days, for example 5 days, without recharging.

Moreover, the charging station 9 has a plug connector 13 for connection to an electrical power network such that a rechargeable battery 12 contained in the charging station 9 can be recharged via the public power net, for example over night. The energy storing facility 12 of the charging station 9 can be arranged in a user-accessible battery compartment such as to be exchangeable. However, it is preferable for the energy storing facility 12 to be a rechargeable battery 6 that is incorporated into the charging station 9 such as to be user-inaccessible. The charging station 9 can be used "on the road" as well, i.e. without access to an electrical power network, for charging the rechargeable battery 6 of the pump unit 4. Therefore, the charging station 9 is set up for this purpose in that the energy for charging the rechargeable battery 6 of a pump unit 4 coupled to it is taken from the internal energy storing facility 12.

A measuring device 14 for measuring an analyte concentration of a sample of body fluid, in particular for determining the glucose content, can be integrated into the charging station 9. The measuring device 14 can determine the glucose content of a sample of body fluid, for example blood or interstitial fluid, that has been applied to a test strip, for example, by photometric or electrochemical means, and display the glucose content to a user by means of a display facility 15, for example a liquid crystal display. Measuring devices of this type are known to those skilled in the art and are used, for example, by diabetics for measuring their blood sugar level such that further explanations concerning the design of the measuring device 14 that is integrated into the charging station 9 are not needed here.

In order to further increase the user comfort for diabetics, a puncturing device can, in addition, be integrated into the charging station 9 and used by a patient to puncture himself, for example in a finger, in order to obtain a sample of body fluid that can subsequently be tested by the measuring device 14.

The charging station 9 has user-actuated operating elements 16, for example keys, which can be used by a user to operate the measuring device 14 that is integrated into the charging station 9, and, in particular, to enter control commands for controlling the pump unit 4.

In operation, the charging station 9 communicates in a wireless manner with the pump unit(s) 4 of the infusion system. For this purpose, the charging station 9 has a transmitter 17 and the pump station 4 has a receiver 18. In order to be able to utilize the advantages of two-way communication, the pump stations also have a transmitter and the charging station also has a receiver, for example in the form of a Bluetooth interface. The use of characteristic identification codes allows the charging station 9 to specifically address an individual pump unit 4, for example the pump unit 4 that is currently carried on the body of the patient together with a cannula carrier unit 1, and to exchange information with it. By this means, the infusion rate at which the pump unit 4 dispenses the liquid medicinal agent to the patient can be preset by a user via the charging station 9. It is also feasible that the charging station analyzes measuring results concerning the glucose concentration or any other analyte concentration of a sample of body fluid that are determined by the integrated measuring device 14, using a control unit, for example in the form of a microprocessor, and controls the infusion rate as a function of these measuring results.

Another option for the communication between the pump unit(s) 4 and the charging station 9 is that a data transfer from the pump unit 4 to the charging station 9 is triggered by placing the pump unit 4 against the charging station 9. Doing so avoids the energy-consuming transmission of data of a pump unit 4 that is carried on the body to a charging station 9 and allows the pump unit 4 to be provided to be particularly compact. For example, transmitter and receiver in the pump unit 4 can be dispensed with and a contact field that is in electrical contact with a contact field of the charging station 9 when the pump unit 4 is charged and thus effects the attachment of a data line can be used for data transmission. It is also feasible to effect the data transmission between pump unit 4 and charging station 9 in an inductive manner or by means of infrared radiation.

The pump unit 4 contains one or more sensors for monitoring its operating status. One possible embodiment provides the pump unit 4 to report its operating status to the charging station 9 such that, for example, malfunctions or a low battery charge of the rechargeable battery or a low liquid level status of the storage volume can be indicated to a user by means of a warning signal. Therefore, the charging station 9 preferably has an acoustical signal facility 19 for generating signal sounds. Alternatively or in addition, the pump unit 4 can also be equipped with a signal facility, in particular an acoustical signal facility, in order to alert a user to a malfunction and/or low battery charge or liquid level status, if applicable. The pump unit can, in particular, also have a sensor for monitoring the filling level of the storage volume 7. If the filling level drops below a given threshold value, this can be signaled to a user by the pump unit 4 generating a corresponding signal. A signal of this type can be generated by the pump unit, for example, as an acoustical signal that can be heard by a user. However, it is also feasible that the pump unit 4 transmits an electromagnetic signal to the charging station 9 which indicates the low filling level to a user by means of an acoustical signal or a light signal.

Moreover, the charging station 9 can have an electronic memory in which user data, in particular measuring results and administered infusion quantities, can be stored. The infusion system described above can be combined with injection systems, for example commercially available insulin pens (pen-shaped injection devices for the insulin administration) to cover a transient peak need. For this purpose, the charging station 9 can be equipped with a receptacle for an injection device, in particular an insulin pen, such that the injection device can be refilled/charged with the agent to be injected and/or energy in the charging station.

It is also feasible, in particular, to use the charging station 9 as data distributor of a system for the treatment of chronic diseases, for example diabetes. For example, the charging station can be set up to exchange data with a separate measuring device, in particular a blood sugar measuring device, and/or a separate injection device, for example an insulin pen. In the process, data of various system components that are important for treatment, in particular measuring results and infusion data, can be collected and stored in the charging station 9. The charging station 9 can either analyze this data by itself or, preferably, pass it on to an analytical device, for example a PC. The data analysis can, in particular, proceed in a separate measuring device, for example a blood sugar measuring device. In this context, it is not necessary to collect all important data in charging station 9, since important data that is not needed by charging station 9 is also generated in the measuring device itself.

The charging station 9 can, in particular, also serve for charging rechargeable batteries of other system components, for example measuring device and/or injection device, and, in this context, receive or supply data from and to these system components, which can, in particular, have their own data memories.

Figure 2:
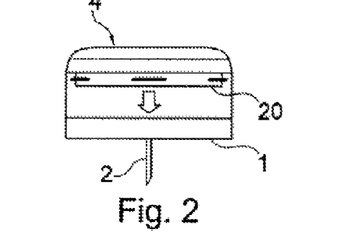
FIG. 2 shows a side view of an embodiment of a pump unit and of an embodiment of a matching cannula carrier unit.
Figure 3:
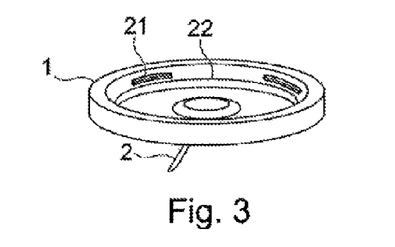
FIG. 3 shows an oblique view of the cannula carrier unit shown in FIG. 2.

FIG. 2 shows an exemplary embodiment of a cannula carrier unit 1 as well as an embodiment of a pump unit 4 of the infusion system described previously that can be attached to it. FIG. 3 shows an oblique view of the cannula carrier unit 1 shown in FIG. 2. The pump unit 4 is attached to the cannula carrier unit 1 in a positive-fit manner, by means of a revolving motion in the embodiment shown. The coupling of the infusion cannula 2 to the storage volume 7 of the pump unit 4 can be effected, for example, in the manner described in WO 2004/026375 A1 by means of a revolving joint with discrete locking positions. In particular a screw locking or bayonet locking is suitable. For this purpose, the pump unit 4 has one or more connection elements 20 which are shown in FIG. 2 and cooperate with one or more connection elements 21 of the cannula carrier unit 1 that are shown in FIG. 3. In the embodiment shown in FIGS. 2 and 3, the pump unit 4 and the cannula carrier unit 1 form an infusion device with a liquid-tight housing.

Between the pump unit 4 and an attached cannula carrier unit 1 acts a seal 22 that can, for example, be provided in the form of a sealing ring shown in FIG. 3 that can be secured to the cannula carrier unit 1.

Figures 4, 5:
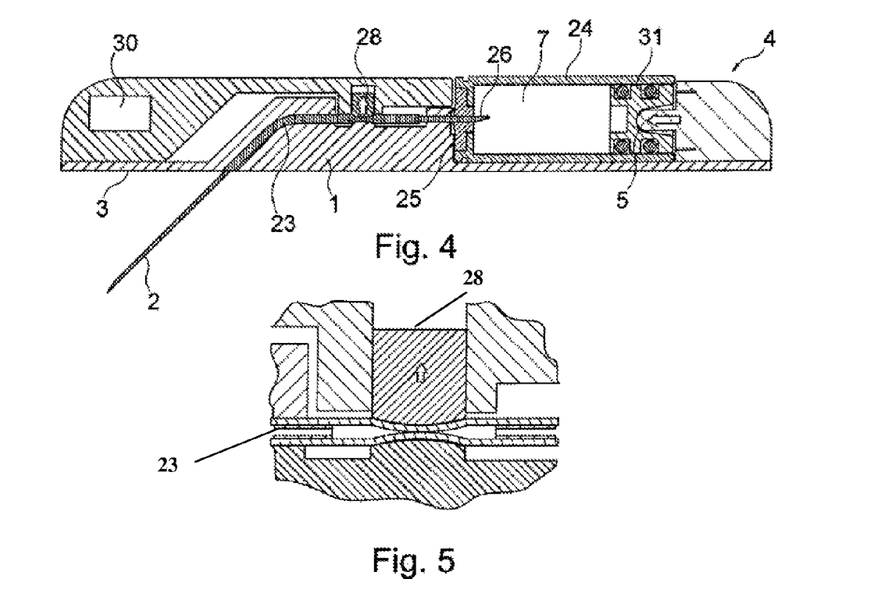
FIG. 4 shows a sectional view of another embodiment of a pump unit with an embodiment of a cannula carrier unit attached to it.
FIG. 5 shows a detail view of FIG. 4.

FIG. 4 shows another embodiment of a pump unit 4 with an embodiment of a cannula carrier unit 1 of the infusion system described previously attached to it. The cannula carrier unit 1 has an infusion cannula 2 for puncturing into the body of the patient as well as a contact surface 3 which, according to purpose, can be placed on the skin of a patient. If the cannula carrier unit 1 is attached to a pump unit 1, as shown in FIG. 4, a liquid line 23 leads from the infusion cannula 2 to the storage volume 7 of the pump unit 4, in which the medicinal agent to be administered is placed. In the embodiment shown, said liquid line 23 is part of the cannula carrier unit 1. In the embodiment shown, the storage volume 7 of the pump unit 4 is provided for receiving an exchangeable medicinal agent vial 24. The medicinal agent vial 24 is closed off by a septum 25, which gets punctured by a transfer cannula 26 of the cannula carrier unit 1 arranged on the end of the liquid line 23 once the pump unit 4 gets attached to the cannula carrier unit 1. Modern septa can easily be punctured many times by a cannula without becoming leaky.

Providing the storage volume such that it receives a medicinal agent container that can be filled multiply in the charging station is advantageous in that said medicinal agent container can be exchanged upon need, for example if signs of wear are evident. As a matter of principle, the storage volume 7 of the pump unit 4 can just as well be a fixedly incorporated tank.

The pump unit 4 possesses a pressure sensor 28 for monitoring an infusion pressure of the liquid medicinal agent. This infusion pressure is measured in the liquid line 23 in the exemplary embodiment shown. In this context, the pressure sensor 28 is provided such that it detects an infusion pressure-effected expansion of a section of tubing through which, according to purpose, the medicinal agent to be administered flows from the storage volume 7 to the infusion cannula 2 of a cannula carrier unit 1. The sensor 28 is shown schematically in FIG. 5, which shows a detailed view related to FIG. 4.

FIG. 5 shows the section of the liquid line 23 that is formed by tubing whose expansion is detected by the pressure sensor 28. In the embodiment shown, the pressure sensor 28 comprises a probing element that is shifted in the direction of the arrow shown in FIG. 5 upon expansion of the section of tubing. The shift is detected and converted into an electrical sensor signal. The pressure sensor 28 could just as well detect an expansion of the liquid tubing, for example, by a capacitance measurement. For this purpose, an external surface of the tubing and an opposite sensor surface of the pressure sensor can form a capacitor whose capacitance changes upon expansion of the section of tubing.

The sensor signal generated by the pressure sensor 28 is analyzed by control electronics 30 that is contained in the pump unit 4. The control electronics 30 generates control signals for controlling the pump 5 as a function of pressure data that are determined from the sensor signal. Blockade of the liquid line 23, for example by a blood clot at the exit of the infusion cannula 2, can be recognized by this means by an increasing liquid pressure. If the liquid pressure reaches a critical upper limit, the pump unit 4 can be turned off by the control electronics 30 and a warning signal can be transmitted to the charging station 9. The charging station 9 then generates a warning signal in order to alert a user of the critical increase of the infusion pressure such that appropriate counter-measures can be undertaken.

The pump 5 of the pump unit 4 has a plunger 31 that gets inserted into the storage volume 7, which can be provided, for example, as a tank or, like in the embodiment shown, for receiving a vial 24, in order to press out the medicinal agent. Suitable pumps are known, for example from WO 01/72358 A1 or DE 100 48 220 A1.

Figure 6:
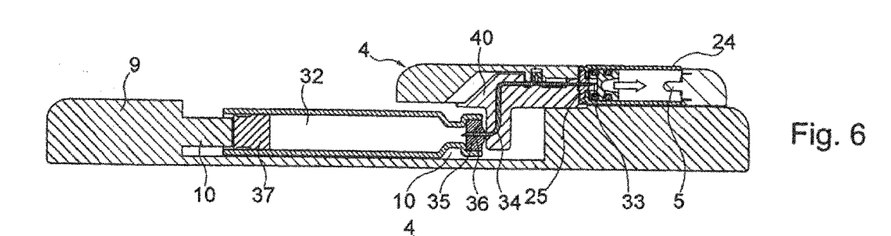
FIG. 6 shows a sectional view of the embodiment of a pump unit with an embodiment of a cannula carrier unit attached to it shown in FIG. 4.
Figures 7, 8:
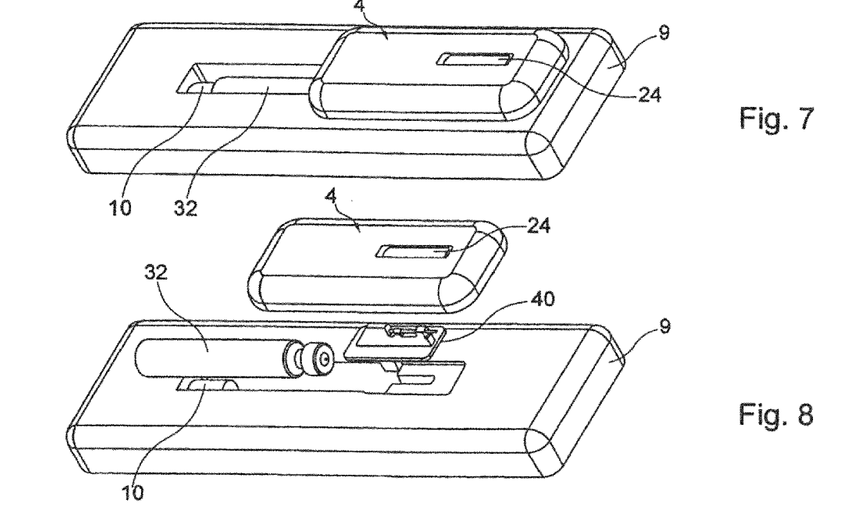
FIG. 7 shows an oblique view related to FIG. 6.
FIG. 8 shows an exploded view related to FIG. 7.

FIG. 6 shows the pump unit 4 described previously, together with an embodiment of a corresponding charging station 9 to which the pump unit 4 is attached. FIG. 7 and FIG. 8 show a schematic oblique view related to FIG. 6 and an exploded view related to FIG. 7, respectively. The charging station 9 has a receiving compartment 10 for a storage container 32 containing the medicinal agent to be administered. The volume of the storage container 32 is preferably selected such that the storage volume 7 of the pump unit 4 can be filled at least three times, preferably four to six times, using it. In the embodiment shown, the storage container 32 is a vial with a volume of 3.2 ml such that the storage volume 7 of the pump unit 4, which is 0.8 ml for example, can be filled four times.

In the embodiment shown, the storage container 32 inserted into the charging station 9 is coupled to the storage volume 7 of the pump unit 4 in the same manner as the infusion cannula 2 of the cannula carrier unit 1 that is intended for puncturing into the body of the patient, namely by having a transfer cannula 33 that is arranged at the end of a liquid line 34 puncturing the septum 25 of a vial 24 that is inserted into the storage volume 7. The septum 35 of a storage container 32 that is inserted into the charging station 9 is punctured by a transfer cannula 36 in corresponding manner such that the storage container 32 is attached to the storage volume 7 of the pump unit 4 via the liquid line 34.

The charging station 9 contains a pump 11 (FIG. 1) that presses liquid from the inserted storage container 32 in order to fill the storage volume 7. The pump 11 of the charging station 9 can be structured alike the pump 5 of the pump unit 4, i.e. have a plunger 31 that is used to push a plug 37 into the storage container 32 in order to press out liquid that is contained therein.

The liquid line 34 that is used for filling the storage volume 7 of the pump unit 4 has essentially the same structure as the liquid line 23 of the cannula carrier unit 1 such that the pressure sensor 28 of the pump unit 4 can also be used to monitor the liquid pressure while the storage volume 7 is being filled. Pressure data determined from the sensor signal of the pressure sensor 28 are transmitted from the pump unit 4 to a control unit of the charging station 9 that controls the pump 11 of the charging station 9 as a function of the pressure data it receives and generates a warning signal in case of a malfunction to allow a user to intervene in a correcting manner if the need arises.

In the embodiment shown in FIGS. 6 to 8, the liquid line 34 of the charging station 9, much like the transfer cannulas 33, 36, is part of an exchangeable transfer module 40 of the charging station 9. This measure is advantageous in that the relatively wear-sensitive transfer line 34 with the transfer cannulas 33, 36 can be exchanged with little effort if the need arises.

Figure 9:
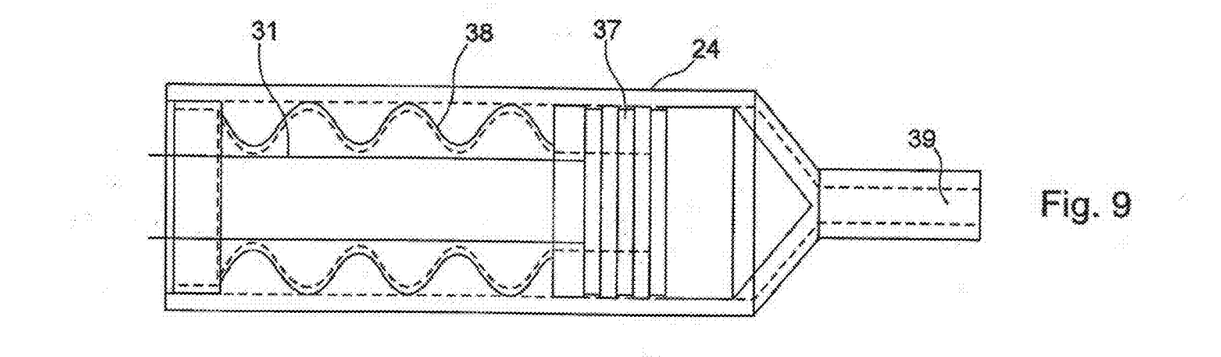
FIG. 9 shows a detailed view of a pump plunger in the process of pressing out a medicinal agent liquid.

FIG. 9 shows a detailed view of an embodiment of a medicinal agent vial 24 that is inserted into the storage volume 7 of the pump unit 4. The re-fillable vial 24 for storage of a medicinal agent has a front end with an opening 39 for passage of the medicinal agent, and a back end that is closed off by means of a shiftable plug 37. The plug 37 is pushed into the vial 24 by the plunger 31 in order to press-out the medicinal agent contained in the vial 24. A bellows 38 is positioned on the plug 37 as a sterile protective cover that surrounds the plunger 31 and protects the internal walls of the vial 24 from contamination. In the exemplary embodiment shown, the bellows 38 is secured in a liquid-tight manner at the back end of the vial 24 and on the plug 37, for example by means of gluing.

The pump unit 4 can just as well be provided for receiving a medicinal agent container that is not provided in the form of a vial. For example, the medicinal agent container 24 can be provided as edge-sealed bag or tube. Instead of a pump 5 that pushes a plunger 31 into a vial 24 in order to press out the medicinal agent like in the embodiment shown, for example a roller or piston pump can be used if other medicinal agent containers are used.

Figure 10:
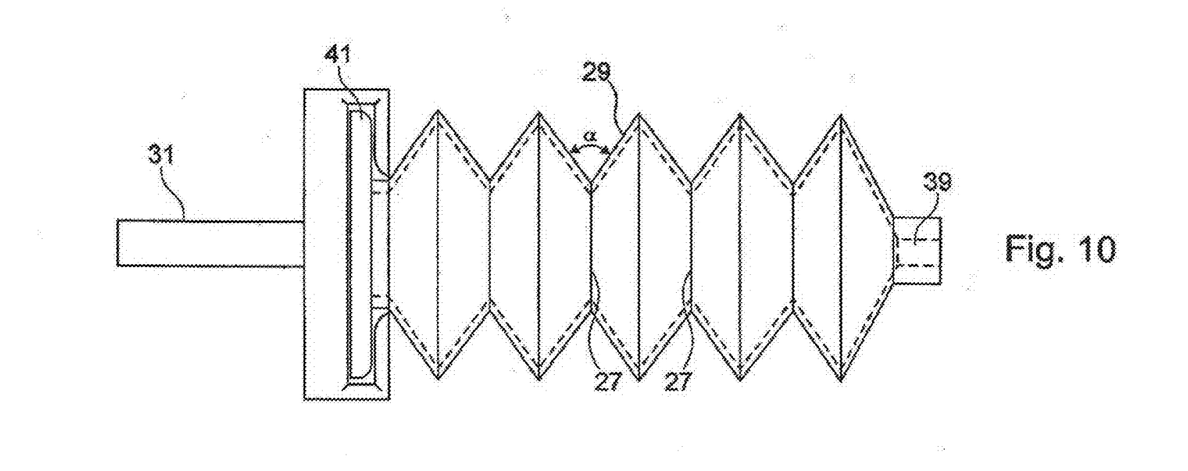
FIG. 10 shows a detailed view of another embodiment of a medicinal agent container of the infusion system.

Another possibility is to provide the medicinal agent container as bellows bag 29 in accordance with FIG. 10. A bellows bag is a refillable edge-sealed bag that has an opening 39 at its front end for passage of the medicinal agent and circumferential plies 27 much like a bellows. When the bellows bag 29 gets filled, the plies 27 unfold such that their opening angle α increases, up to 180° in the extreme case, whereby the length of the bellows bag increases. In order to remove liquid from the bellows bag 29, said bellows bag is pushed together by the pump rod 31. This shortens the bellows bag and the opening angle α of the plies 27 is reduced, until the plies 27 are fully closed in the extreme case, i.e. the opening angle α is reduced to zero. FIG. 10 is idealized with respect to how it shows the plies 27 in order to illustrate the principle. In real bellows bags, the plies 27 are less pronounced and can, in the extreme case, take on the shape of waves such that the appearance of a bellows bag can resemble a corrugated pipe.

Bellows bags are known for the storage of liquid medicinal agents, for example eye-drops, and can be manufactured in a cost-efficient manner using so-called blow-fill seal procedures.

The bellows bag 29 shown in FIG. 10 is fabricated from polyethylene. For coupling to the pump rod 31, it is provided with a coupling element in the form of an undercut head 41 that gets inserted into a matching receptacle of the pump rod 31.

Figure 11:
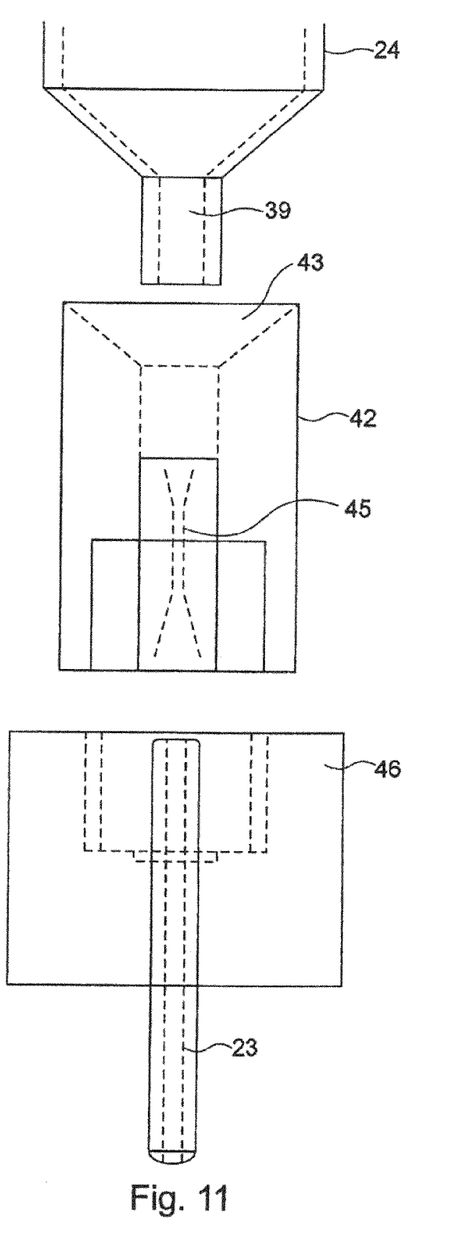
FIG. 11 shows another embodiment of a mechanism for attaching a medicinal agent container to the liquid line of the cannula carrier unit or charging station.

In the embodiment shown in FIGS. 4 and 6, the storage volume 7 of the pump unit 4, which can, for example, be an inserted medicinal agent container or a fixedly incorporated tank, is attached to the liquid line 23 and/or 34 of the cannula carrier unit 1 and/or the charging station 9 by means of a transfer cannula 26 and/or 33, respectively, that punctures a septum 25. An alternative possibility of attachment is shown in FIG. 11. The opening 39 of the medicinal agent container 24 and/or of an incorporated tank is provided in the form of a section of pipe onto which a coupling piece 42 is placed with one of its ends. The coupling piece 42 is matched exactly in its dimensions to the external diameter of said section of tube such that a tight connection results. In addition, the coupling piece 42 has a funnel-shaped recess 43 that matches a cylinder-shaped stud 44 of the medicinal agent container 24 and/or tank such that the internal surface of the recess 43 of the coupling piece rests with its surface against the stud 44 whose middle transitions into the section of tube and, by this means, increases the mechanical strength of the connection to the coupling piece.

The coupling piece 42 contains a connection piece 45 made of an elastomeric material of a type that is commonly used in the application range of sterile liquids. The connection piece 45 has two funnel-shaped openings. On the inside is situated a longitudinal channel that is opened only upon the capillary liquid line 23 being pushed into it. The connection piece 45 then rests against the opening 39 of the medicinal agent container 24. This means improves the hygiene during detaching and re-connecting. As an additional measure to improve the reliability of the connection, the liquid line 23 can be provided with an end-piece 46 that forms a plug connection with the coupling piece 42.

Figure 12:
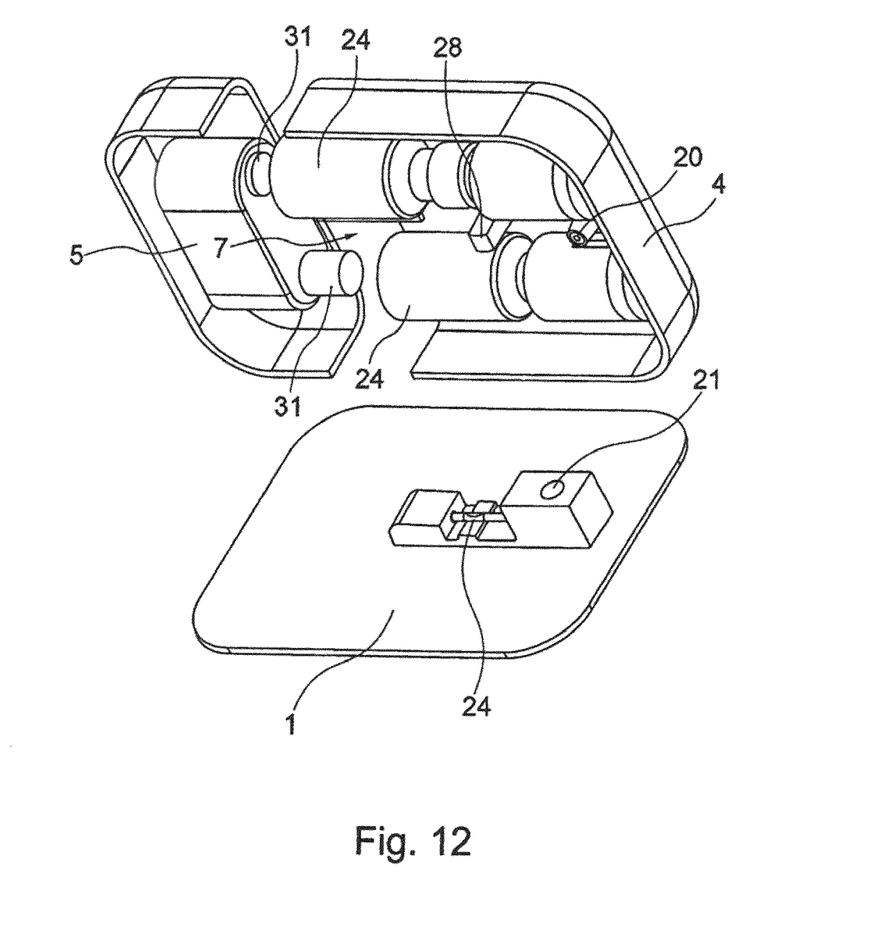
FIG. 12 shows another embodiment of a pump unit and matching cannula carrier unit.

FIG. 12 shows another embodiment of a pump unit 4 with a matching exemplary embodiment of a cannula carrier unit 1. The pump unit 4 can be secured on the cannula carrier unit 1 in a detachable manner by means of connection elements 20, 21. The connection elements 20, 21 effect a non-positive fit connection in the embodiment shown. For this purpose, one connection element 20 is formed by a conical peg that engages in a bushing that forms the corresponding connection element 21. The essential difference between the pump unit 4 shown in FIG. 9 and in the embodiments described previously is that the storage volume 7 of the pump unit 4 is designed for receiving two medicinal agent vials 24. The pump unit 4 has for each of the two medicinal agent vials 24 one pump plunger 31 that gets inserted into said vials in order to press out liquid that is contained in the medicinal agent vials 24.

The pump unit 4 contains a liquid line that facilitates attachment of the vials 24 to the infusion cannula of the cannula carrier unit 1 via two branching sites (not shown). In operation, the pump unit 4 first presses liquid out of only one of the two medicinal agent vials 24. Only when said vial is empty, liquid is removed from the second medicinal agent vial 24. Once an inserted medicinal agent vial 24 is empty, the pump unit 4 generates a signal to alert a user to this status allowing him to exchange the empty medicinal agent vial 24 before the second medicinal agent vial 24 is empty also.

In this embodiment, a charging station 9 can, as a matter of principle, be dispensed with provided an energy storing facility with a sufficient storage capacity is present in the pump unit. However, the use of rechargeable batteries and a charging station 9 is advantageous in this exemplary embodiment. In particular, a single pump unit 4 is, as a matter of principle, sufficient for a patient, since the patient replaces either of the two medicinal agent vials in the pump unit according to need. Having a pump unit 4 with a receptacle for two medicinal agent vials 24 allows the patient to freely select the point in time of vial replacement over a convenient time window of several hours without wasting any of the valuable content of the medicinal agent vials 24.

Therefore, one aspect of the invention relates to an infusion system for administering a liquid medicinal agent, in particular insulin, having a pump unit 4 that can be attached to an infusion cannula and comprises a pump 5, an electrical energy storing facility for supplying energy to the pump 5, and two receptacles into which one vial 24 each containing the medicinal agent can be inserted.

Thus, embodiments of the infusion system are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. An infusion system for administering a liquid medicinal agent, in particular insulin, comprising:
    a cannula carrier unit comprising an upper side facing away from a body of a patient with a transfer cannula contained within the cannula carrier unit, an under side with an adhesive for directly securing the under side to the body of the patient and the under side is coupled to the transfer cannula, and an infusion cannula for puncturing into the body of the patient, the infusion cannula extending directly from the under side without being outside the perimeter of the under side;
    a pump unit removably connected to the upper side of the cannula carrier unit using a positive-fit, the pump unit comprising a pump, a rechargeable battery for supplying energy to the pump, and a medicinal agent container being non-removable from the pump unit carried in a storage volume of the pump unit coupled to the transfer cannula, wherein the pump unit rests on the upper side of the cannula carrier unit after attachment of the pump unit to the cannula carrier unit; and
    a charging station configured to receive the pump unit detached from the cannula carrier unit using a positive-fit to both recharge the rechargeable battery and refill the medicinal agent container with the liquid medicinal agent to be administered.

2. The infusion system according to claim 1, wherein the pump unit comprises two pump units configured to be charged in the charging station in an alternating manner.

3. The infusion system according to claim 1, wherein the charging station comprises a measuring device for determining an in vitro analyte concentration of a sample of body fluid.

4. The infusion system according to claim 1, wherein the pump unit has a pressure sensor for monitoring an infusion pressure of the liquid medicinal agent.

5. The infusion system according to claim 1, wherein the rechargeable battery is incorporated into the pump unit such as to be inaccessible for a user.

6. The infusion system according to claim 1, wherein the charging station is set up to take energy for charging the rechargeable battery of the pump unit coupled to the charging station from an internal energy storing facility.

7. The infusion system according to claim 1, wherein the pump unit has a sensor for monitoring the filling level of the storage volume.

8. The infusion system according to claim 1, wherein the storage volume comprises a refillable bellows bag for storing the liquid medicinal agent, the bellows bag comprises a front end with an opening for passage of the liquid medicinal agent and a back end with a coupling element for positive-fit coupling to a pump rod.

9. The infusion system according to claim 1, further comprising a refillable vial for storing the liquid medicinal agent, the refillable vial comprises a front end with an opening for passage of the liquid medicinal agent and a back end that is closed off by a shiftable plug, wherein a bellows is secured to the shiftable plug and protects internal walls of the vial from contamination when the shiftable plug is being pushed into the vial.

10. An infusion system for administering a liquid medicinal agent, in particular insulin, comprising:
    two pump units, which each comprise a pump, a rechargeable battery, an a medicinal agent container that is non-removable carried in a storage volume of each pump unit, wherein each pump unit is removably attachable to a cannula carrier unit upper side using a positive-fit facing away from the body of a patient with a transfer cannula contained within the cannula carrier unit of the infusion system such that the pump rests on the cannula carrier unit after attachment of the pump unit to the cannula carrier unit; and
    a charging station configured to receive each of the pump unit in an alternating manner such that when one of the pump unit is received in the charging station using a positive-fit, the charging station both recharge the rechargeable battery and refill the medicinal agent of the pump unit.

11. The infusion system according to claim 10, wherein the storage volume comprises a refillable bellows bag for storing a liquid medicinal agent, the bellows bag comprises a front end with an opening for passage of the medicinal agent and a back end with a coupling element for positive-fit coupling to a pump rod.

12. The infusion system according to claim 10, further comprising a refillable vial for storing a liquid medicinal agent, the refillable vial comprises a front end with an opening for passage of the medicinal agent and a back end that is closed off by a shiftable plug, wherein a bellows is secured to the plug and protects internal walls of the vial from contamination when the plug is being pushed into the vial.

13. The infusion system according to claim 10, wherein the cannula carrier unit is secured to the body of a patient and comprises an infusion cannula for puncturing into the body of the patient.

14. A rechargeable modular insulin infusion system having a fully enclosed infusion line wearable infusion pump, comprising:
- a cannula carrier configured to be directly secured to a body of a patient with an adhesive;
- an infusion cannula carried in the cannula carrier being a few centimeters long, the infusion cannula having a distal end positioned within the cannula carrier and a proximal end in the form of a hollow needle configured for puncturing the body of the patient wherein the proximal end extends directly from an under side of the cannula carrier without being outside the perimeter of the under side;
- a pump unit removably connected to the cannula carrier using a positive-fit, the pump unit having a pump coupled to the infusion cannula distal end and a medicinal agent container non-removable from the pump unit carried in a storage volume of the pump unit having a replenishment connector, and the pump being electrically connected to a rechargeable battery having a recharging connector; and
- a charging station configured to the pump unit removed from the cannula carrier using a positive-fit and both recharge the rechargeable battery and refill the medicinal agent container, the charging station comprising:
  - a plug connector for external power that is electrically coupled to a charging connector that is coupled to the recharging connector to recharge the rechargeable battery, and
  - a receiving compartment for a storage container containing the medicinal agent, and a charging pump for pumping the medical agent from the storage container into the medicinal agent container carried in the pump unit.

15. The rechargeable modular insulin infusion system as in claim 14 wherein the storage volume comprises two medicinal agent containers with each medicinal agent container holding less than or equal to a 12 hour supply of medicinal agent and configured so when one of the two medicinal agent containers is empty the medicinal agent container that is empty can be replaced during a window of time comprising less than 12 hours while the infusion system continues operating using the medicinal agent container that is not empty.

16. The rechargeable modular insulin infusion system as in claim 14 wherein the cannula carrier remains on the body of the patient while the pump unit is placed in the charging station to replenish the medicinal agent.

* * * * *